US007303908B1

(12) United States Patent
Overland

(10) Patent No.: US 7,303,908 B1
(45) Date of Patent: Dec. 4, 2007

(54) BIOREMEDIATION ASSEMBLY

(75) Inventor: Bert A. Overland, Spokane, WA (US)

(73) Assignee: Surface Technologies IP AG (CH)

( * ) Notice: Subject to any disclaimer, the term of this patent is extended or adjusted under 35 U.S.C. 154(b) by 128 days.

(21) Appl. No.: 11/495,275

(22) Filed: Jul. 27, 2006

(51) Int. Cl.
*C12M 1/02* (2006.01)
*C12M 1/04* (2006.01)
*B08B 1/08* (2006.01)

(52) U.S. Cl. ............................... 435/289.1; 435/301.1; 435/812; 435/818; 134/108; 134/111

(58) Field of Classification Search ............ 435/289.1, 435/301.1, 812, 818
See application file for complete search history.

(56) References Cited

U.S. PATENT DOCUMENTS 4,244,815 A * 1/1981 Chaikin et al. ............. 210/622
5,961,733 A * 10/1999 Strange ....................... 134/10
6,057,147 A 5/2000 Overland et al.
7,128,075 B2 * 10/2006 Publ ........................... 134/107

FOREIGN PATENT DOCUMENTS

JP 01301895 A * 12/1989

* cited by examiner

*Primary Examiner*—William H. Beisner
(74) *Attorney, Agent, or Firm*—Wells St. John P.S.

(57) ABSTRACT

A bioremediation assembly and method for bioremediation are described and which includes a bioremediation reservoir defining a cavity; a pump mounted within the bioremediation reservoir and which removes the aqueous bioremediating fluid from the bioremediation reservoir; and a fluid dispensing manifold positioned within the bioremediation reservoir and which is coupled in fluid flowing relation relative to the pump, and which directs a stream of bioremediating fluid downwardly so as to aerate the volume of bioremediating fluid.

22 Claims, 8 Drawing Sheets

BIOREMEDIATION ASSEMBLY

TECHNICAL FIELD

The present invention relates to a bioremediation assembly, and a method for bioremediation, and more specifically to a bioremediation assembly which includes a reservoir having a discrete geometry, and a fluid dispensing manifold which is positioned in fluid dispensing relation relative to the reservoir and which, when operated in an aeration mode, directs a stream of bioremediating fluid onto the top surface of the bioremediating fluid which is in the reservoir, so as to create small air bubbles which are drawn through the bioremediating fluid by the action of a pump so as to aerate a microbial population which resides in same.

BACKGROUND OF THE INVENTION

The beneficial effects of employing a bioremediation assembly is disclosed in my U.S. Pat. No. 6,057,147 which issued on May 2, 2000. In that earlier U.S. patent, I disclosed an apparatus and method for bioremediation of hydrocarbon contaminated objects which included a reservoir which acted as a biochamber and which accelerated the bioremediation of oil/grease contamination encountered in parts used, for example, in automobile, aircraft and small engine industries where numerous objects are typically contaminated with oils and/or greases. That invention further described a method for cleaning hydrocarbon-contaminated objects by degrading the hydrocarbon constituents of petroleum products through a process of enhanced bioremediation.

While the invention described in U.S. Pat. No. 6,057,147 has worked with a great deal of success, several shortcomings have detracted from its usefulness. One difficulty associated with all of the prior art designs has been the proper aeration of the bioremediation fluid so as to encourage the continued growth of the microorganisms contained therein. Still further, another difficulty associated with many of the prior art devices has been the appropriate heating of the bioremediating fluid so as to maintain the bioremediating fluid within a proper temperature range so as to encourage the growth of the microorganisms which degrade the petroleum or other hydrocarbon products which are received therein.

A bioremediation assembly and method of bioremediation which addresses these, and other issues are the subject matter of the present application.

SUMMARY OF THE INVENTION

A first aspect of the present invention relates to a bioremediation assembly which includes a bioremediation reservoir defining a cavity and which encloses a volume of an aqueous bioremediating fluid at a predetermined temperature, and wherein the bioremediation reservoir has a geometry which acts upon the volume of the aqueous bioremediating fluid so as to cause the bioremediating fluid to be maintained at a substantially constant temperature; a pump mounted within the bioremediation reservoir and which is operable to remove the aqueous bioremediating fluid from the bioremediation reservoir; and a fluid dispensing manifold positioned within the cavity of the bioremediation reservoir and located in spaced relation relative to a top surface of the volume of aqueous bioremediating fluid which is enclosed with the bioremediation reservoir, and wherein the fluid dispensing manifold is coupled in fluid flowing relation relative to the pump, and is operable to direct a stream of bioremediating fluid downwardly into the top surface of the bioremediating fluid so as to aerate the volume of bioremediating fluid.

Another aspect of the present invention is a bioremediation assembly, which includes a bioremediation reservoir defined by a continuous sidewall, and a bottom panel which is made integral with the continuous sidewall, and wherein the continuous sidewall defines an upwardly oriented opening, and an internal cavity; a volume of bioremediating fluid received within the internal cavity of the bioremediation reservoir, and wherein the bioremediating fluid has a top surface; a pump mounted on the bottom panel and within the internal cavity of the bioremediation reservoir, and wherein the pump withdraws bioremediating fluid from the bioremediation reservoir, a wash basin having a drain which is mounted in fluid communication with the opening which is defined by the bioremediation reservoir; a fluid applicator positioned in fluid dispensing relation relative to the wash basin; an in-line heater mounted on an outside facing surface of the continuous sidewall, and wherein the in-line heater is coupled in fluid communication with the pump and with fluid applicator, and wherein the heater is located upstream relative to the pump and is operable to heat the bioremediating fluid, and is further located downstream relative to the fluid applicator; and a fluid dispensing manifold mounted within the internal cavity of the bioremediation reservoir and in spaced relation relative to the top surface of the bioremediating fluid, and wherein the fluid dispensing manifold is coupled in fluid flowing relation relative to the pump, and is located downstream relative to the in-line heater, and wherein the fluid dispensing manifold, when operated in an aeration mode, directs a plurality of streams of bioremediating fluid downwardly onto the top surface of the bioremediating fluid so as create small air bubbles which are drawn downwardly through the volume of the bioremediating fluid by the action of the pump and in the direction of the bottom panel.

Another aspect of the present invention is to provide method for bioremediation which includes the steps of providing an object of interest which is coated with a hydrocarbon substance; providing a source of bioremediating fluid which has a top surface; and withdrawing a portion of the bioremediating fluid and forming a stream of bioremediating fluid which alternatively is directed downwardly against the top surface of the bioremediating fluid so as to form small air bubbles, or which is directed against the object of interest so as remove the hydrocarbon substance from the object of interest.

Another aspect of the present invention is to provide a method for bioremediation which includes the steps of providing a bioremediation reservoir with a bottom surface, and an upwardly facing opening and further having a predetermined geometry which defines an internal cavity; supplying a source of a bioremediating fluid to the bioremediation reservoir, and wherein the bioremediating fluid has a top surface; providing a wash basin which is located in gravity draining relation relative to the opening of the bioremediation reservoir; providing a fluid applicator which is mounted on the wash basin; providing a fluid dispensing manifold and positioning the fluid dispensing manifold in spaced, fluid dispensing relation relative to the top surface of the bioremediating fluid and downstream relative to the wash basin; providing a pump which is mounted on the bottom surface of the bioremediation reservoir and which withdraws the bioremediating fluid from the bioremediation reservoir; providing a heater for heating the bioremediating fluid to a given temperature, and which is coupled in fluid receiving relation relative to the pump; providing a valve assembly which is coupled in fluid receiving relation relative to the heater and which is further disposed in selective fluid dispensing relation to the fluid dispensing manifold and the fluid applicator; providing and positioning a porous evaporation barrier in substantially covering relation relative to the opening of the bioremediation reservoir and upstream of the fluid dispensing manifold; and withdrawing the bioremediating fluid from the bioremediation reservoir with the pump and alternatively delivering the heated bioremediation fluid to the fluid dispensing manifold or to the fluid applicator.

These and other aspects of the present invention will be described in greater detail hereinafter.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Figure 1:
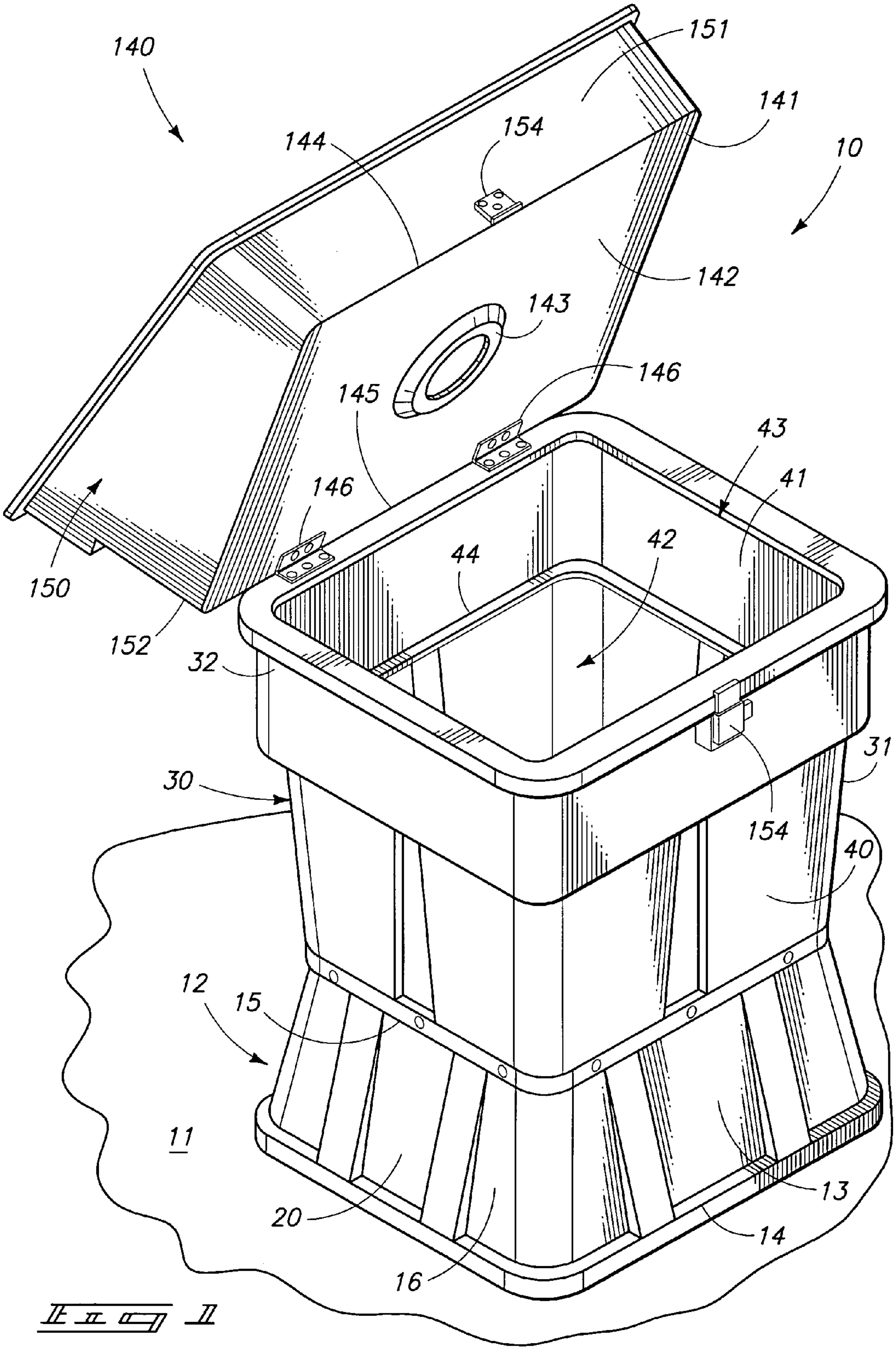
FIG. 1 is a perspective side elevation view of the bioremediation assembly of the present invention shown in an open position, and with some elements removed to show the structure thereunder.
Figure 2:
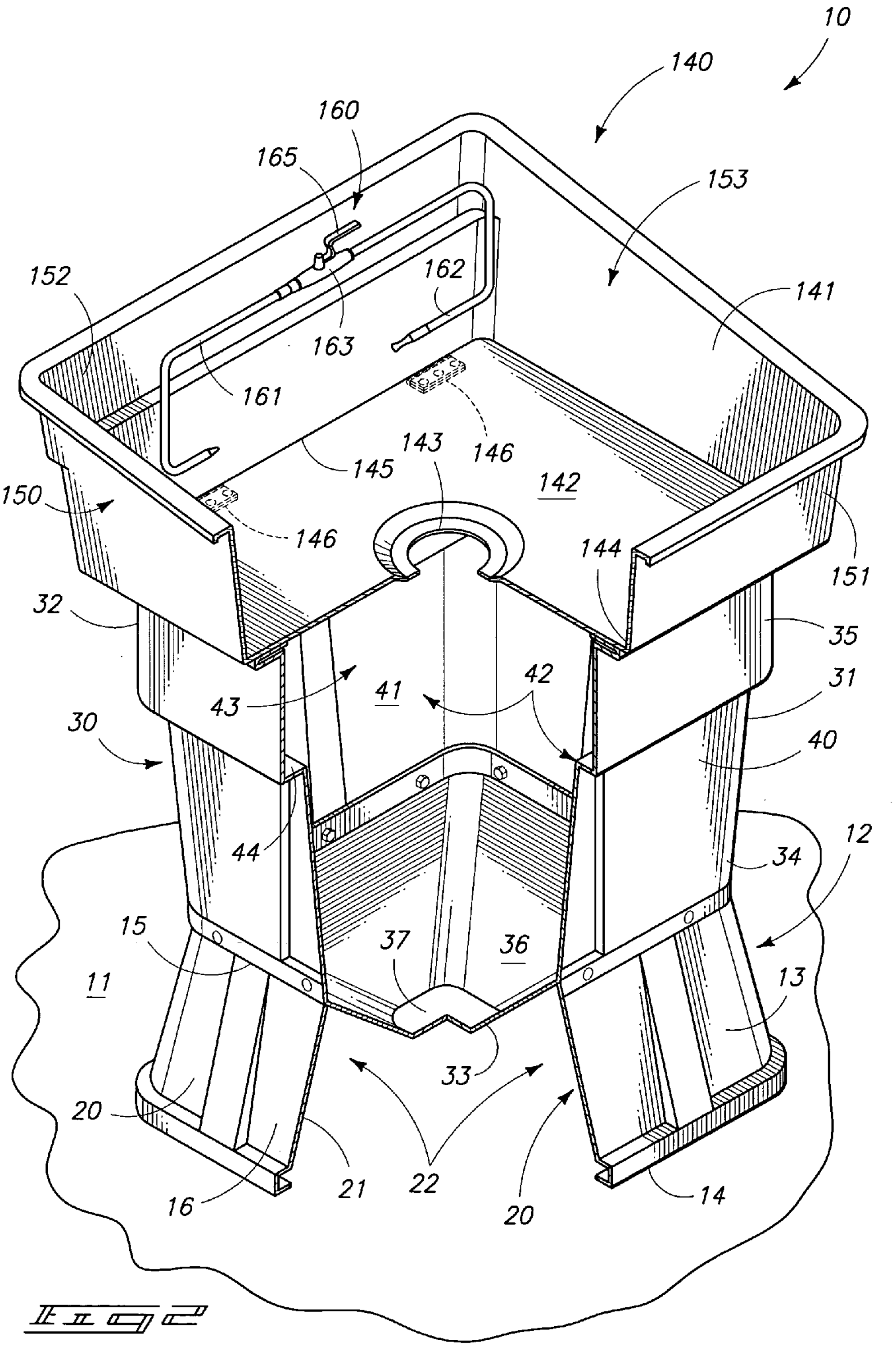
FIG. 2 is a perspective, fragmentary, partial, transverse, vertical sectional view of the bioremediation assembly of the present invention with some elements removed to show the structure thereunder.

A bioremediation assembly of the present invention is generally indicated by the numeral 10 in FIG. 1, and following. As seen in those drawings, the bioremediation assembly 10 can be positioned on a supporting surface or the face of the earth 11 in an upstanding, self supporting orientation, as illustrated. In this regard, the bioremediation assembly 10 has a base portion, which is generally indicated by the numeral 12, and which rests on the supporting surface or face of the earth 11, and which further has a main body 13. The base portion 12 has a first, earth engaging end 14 which provides a firm foundation for the bioremediation assembly 10; and an opposite second end 15. As seen in FIGS. 1 and 2, the base portion 12 has a sidewall 16 which generally forms a generally frusto-pyramidal shape. Still further, the sidewall 16 has an outside facing surface 20, and an opposite inside facing surface 21 which defines a cavity 22 (FIG. 2). The cavity 22 is operable to telescopingly receive a portion of the bioremediation reservoir which will be discussed in greater detail in the paragraphs which follow.

Referring more specifically to FIG. 2 and following, the bioremediation assembly 10 includes a bioremediation reservoir which is generally indicated by the numeral 30. The bioremediation reservoir has a main body 31 which has a first end 32, and an opposite second end 33. As seen in the drawings, the bioremediation reservoir has a diminishing cross-sectional dimension when that cross-sectional dimension is measured from the first end 32, in the direction of the second end 33. As illustrated in the drawings, the main body 31 is defined by a sidewall 34. The sidewall includes a first portion 35 (FIG. 3) which is substantially vertically oriented; and a second portion 36 which is made integral with the first portion 35, and which slopes inwardly towards a substantially flat bottom panel, or surface 37. In this regard, the second portion 36 is substantially frustum-shaped. Still further, as seen in FIG. 2 it will be understood that the second portion 36 is substantially telescopingly received, at least in part, within the cavity 22 as defined by the inside facing surface 21 of the base portion 12. As illustrated in FIG. 2 and following, the sidewall 34 is defined by an outside facing surface 40, and an opposite inside facing surface 41. The inside facing surface 42 defines a cavity. Still further, the first portion 35 defines an upwardly facing opening 43 (FIG. 1) which is disposed in gravity feeding relation relative to a wash basin which will be described in greater detail hereinafter. As should be understood, the bioremediation reservoir 30 has a geometry which acts upon a volume of aqueous bioremediating fluid, as will be described below, so as to cause the bioremediating fluid to maintain a substantially constant temperature. The inside facing surface 41 of the sidewall 34 defines a step or ledge 44 (FIGS. 1 and 2), and which is operable to support other assemblies which will be discussed in greater detail, hereinafter.

Figures 3, 4:
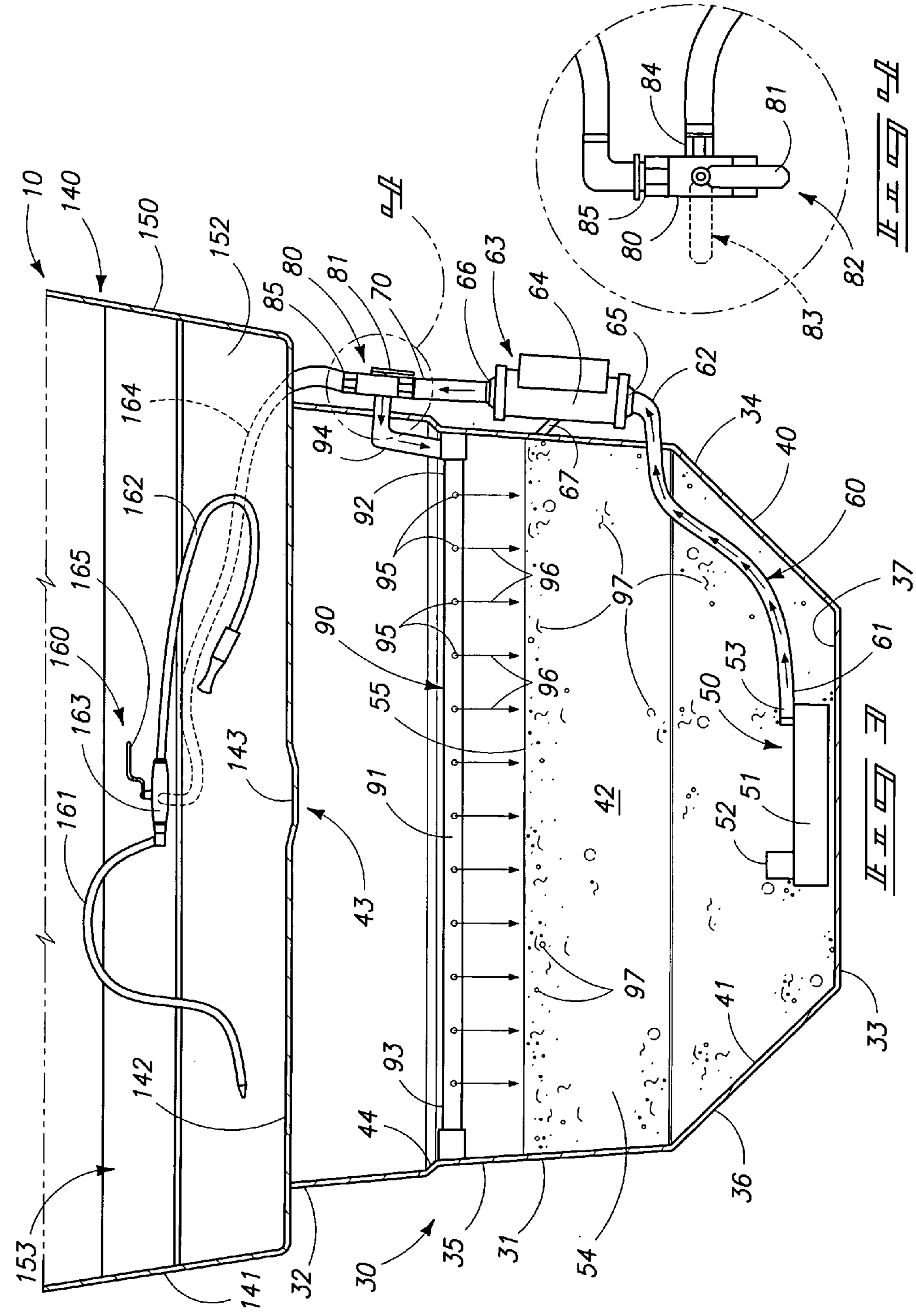
FIG. 3 is a partial, fragmentary, transverse, vertical sectional view of the bioremediation assembly of the present invention, and with some supporting surfaces removed to show the structure thereunder, and further illustrating the flow of bioremediating fluid therethrough and when operating in an aeration mode.
FIG. 4 is a fragmentary, partial, side elevation view of a valve assembly used in the bioremediation assembly of the present invention, and which further illustrates the position of the valve assembly when the invention is operating in an aeration mode.

As best seen by reference to FIG. 3, and following, it will be seen that a pump 50 is mounted on the bioremediation reservoir 30 and positioned within the cavity 42 thereof. As illustrated in FIG. 3 and following, the pump is mounted on the bottom surface 37. As illustrated, the pump has a main body 51 with a first intake end 52, and a second exhaust end 53. Still further, it will be seen by FIG. 3 that a volume bioremediating fluid 54 is received within the cavity 30, and has a top surface 55. As illustrated, it will be understood that the pump 50 is operable to withdraw a portion of the bioremediating fluid 54 by means of the pump 50 and thereafter deliver the source of bioremediating fluid 54 alternatively to a fluid dispensing manifold, or a fluid applicator as will be described in greater detail hereinafter. As best seen by reference to FIG. 7, the pump 50 is energized by means of an electrical conduit 56 which extends upwardly through the bioremediating fluid 54, and through the sidewall 34 of the bioremediation reservoir 30. The bioremediating fluid is a product sold by Natures Way, Inc. and which is marketed under the Trademark PC™. This product is disclosed more fully in U.S. Pat. No. 5,561,059 to Kaiser et al. Further, discussion of this bioremediating fluid is not warranted in the present application.

Figure 5:
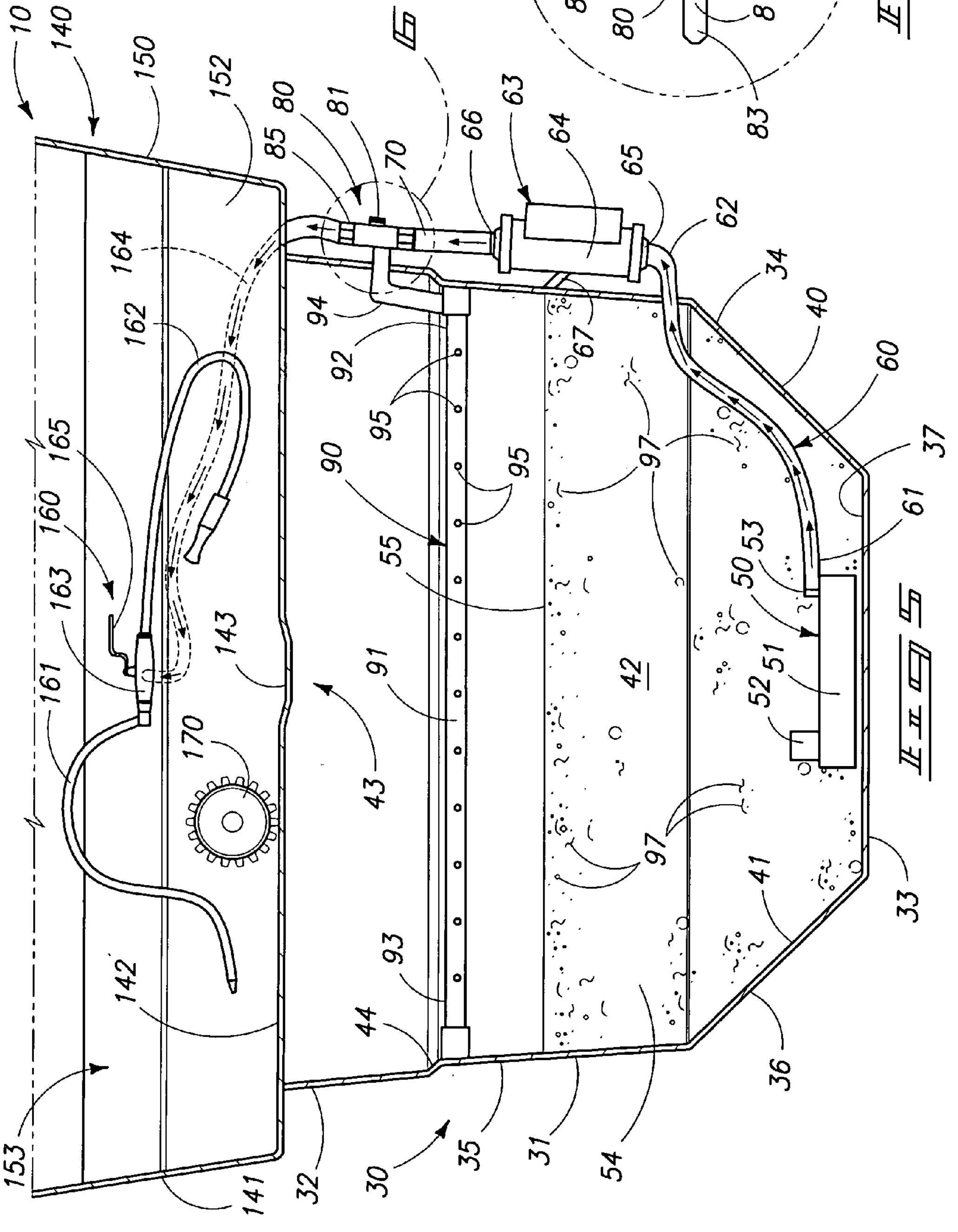
FIG. 5 is a fragmentary, transverse, vertical sectional view of the bioremediation assembly of the present invention and showing the flow of bioremediating fluid therethrough, and the delivery of the bioremediating fluid to a wash basin.
Figure 7:
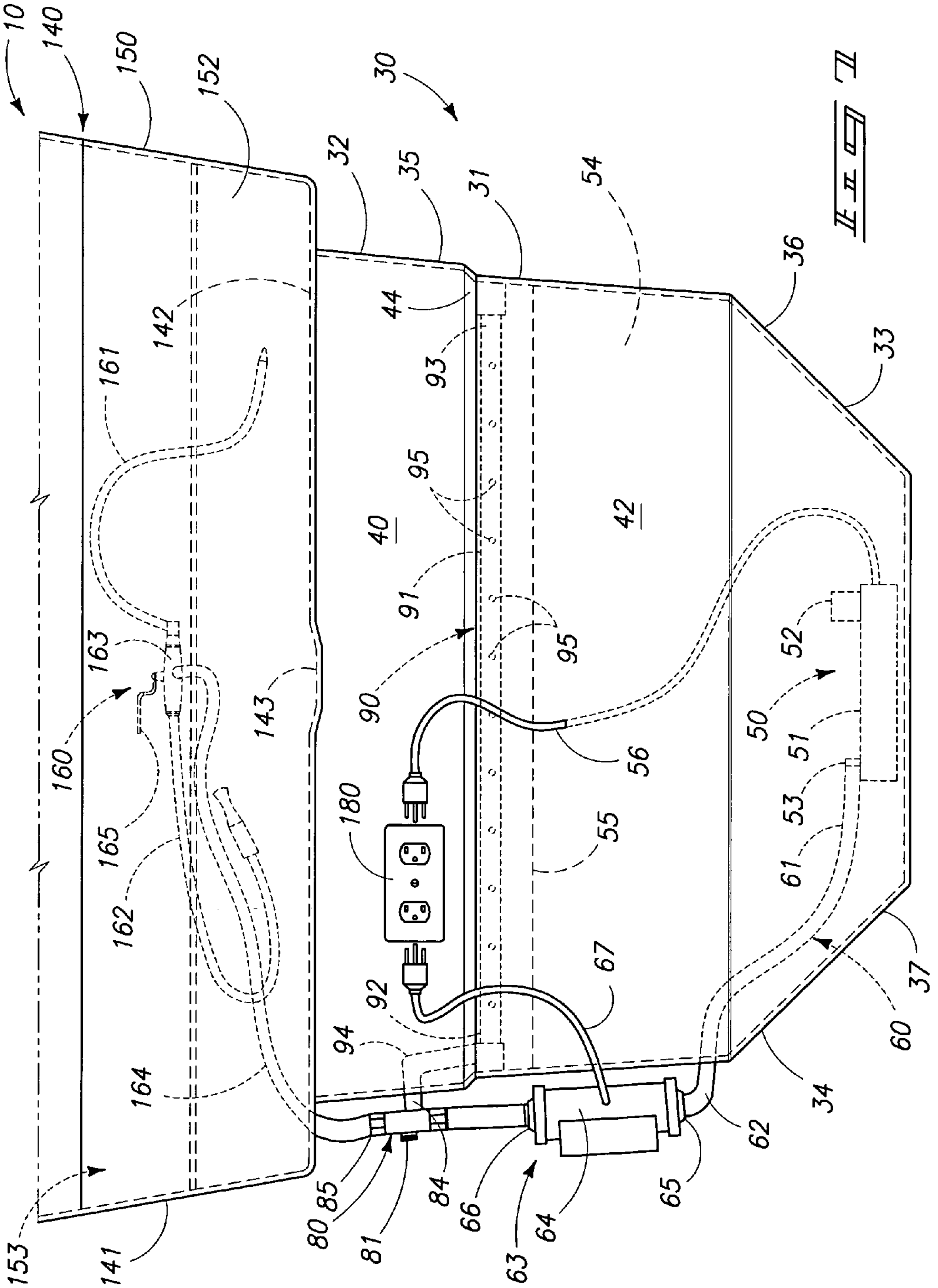
FIG. 7 is a fragmentary, side elevation view of a bioremediation assembly of the present invention, and with some underlying surfaces shown in phantom lines to illustrate the structure thereunder.
Figure 8:
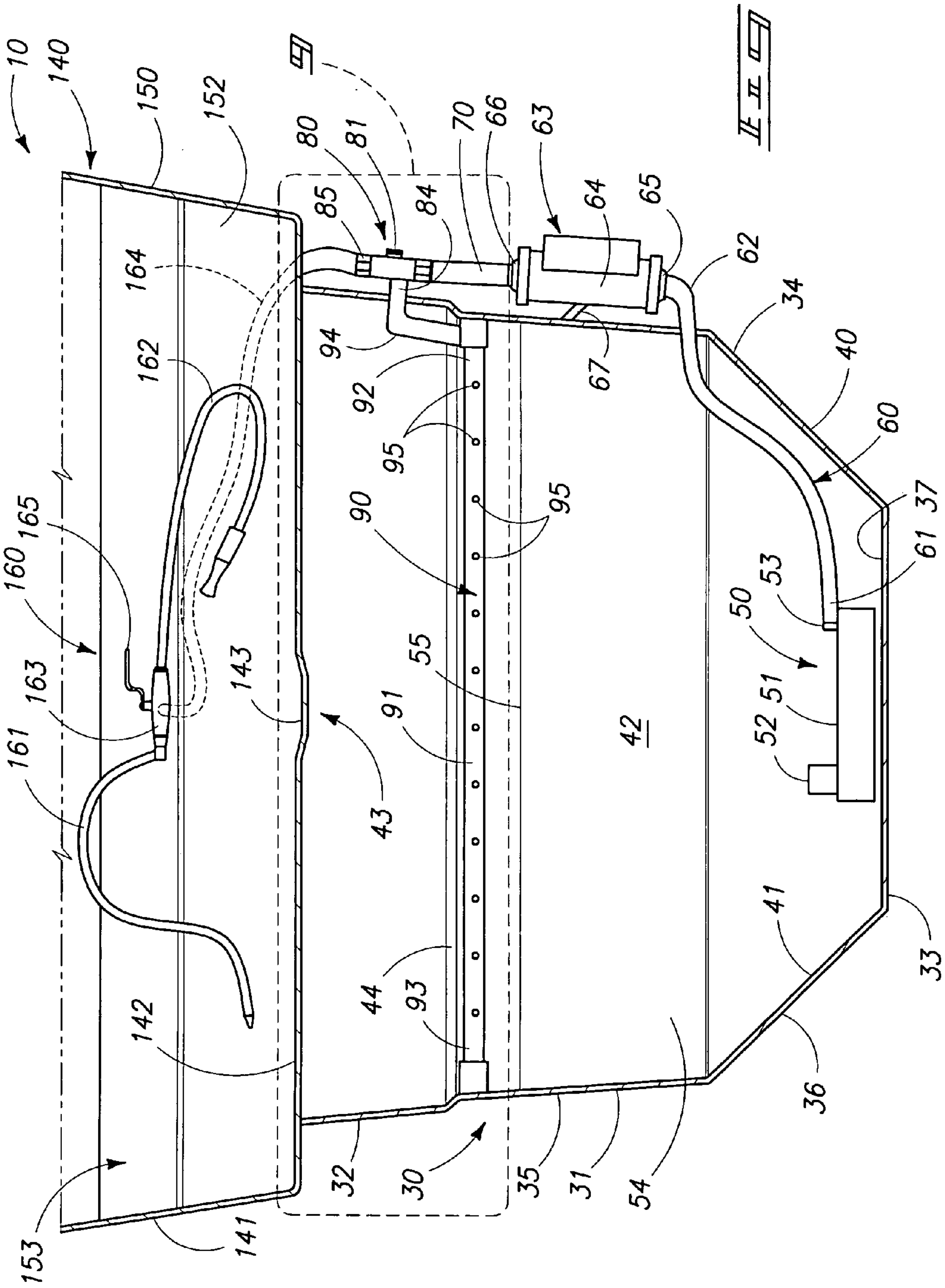
FIG. 8 is a partial, fragmentary, vertical sectional view of the bioremediation assembly of the present invention, and with some surfaces removed to show the structure thereunder.

As illustrated most clearly by reference to FIGS. 3, 5 and 7, the pump 50 further includes a first fluid conduit which is generally indicated by the numeral 60. The first fluid conduit has a first intake end 61, which is coupled in fluid flowing relation relative to the exhaust end 53 of the pump 50, and a second, and opposite exhaust or fluid delivery end 62 which is operable to deliver the bioremediating fluid 54, provided by the pump 50 to an inline heater 63 which is mounted exteriorly relative to the bioremediation reservoir 30. In this regard, the inline heater 63 has a main body 64 which has an intake end 65, which is coupled in fluid flowing relation relative to the second end 62, of the first fluid conduit, and an opposite exhaust end 66. The inline heater 63 is energized by an electrical conduit 67. The inline heater is operable to impart heat energy to the bioremediating fluid 54 which is passing therethrough in order to heat the volume of bioremediating fluid 54 to a temperature of about 105 degrees F. to about 115 degrees F. The inline heater has a fluid pressure sensor, not shown, which is operable to render the inline heater inoperable unless the fluid pressure sensor senses a given fluid pressure as provided by the volume of bioremediating fluid 54. The inline heater also provides a means whereby the bioremediating fluid is prevented from reaching a temperature where it might scald an operator who is employing the bioremediation apparatus 10, or further kill off the microorganisms which are present in the bioremediating fluid 54.

Figure 6:
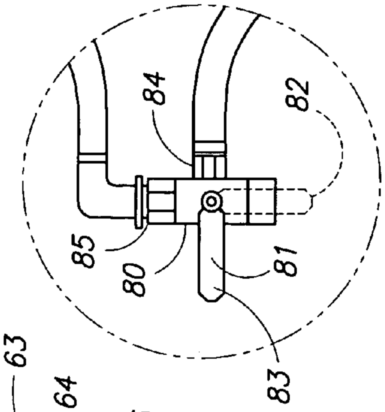
FIG. 6 is a second, fragmentary, side elevation view of a valve assembly used in the bioremediation assembly of the present invention, and which is illustrated in a second position which facilitates the delivery of the bioremediating fluid to the wash basin.

As best seen in FIGS. 3-9, it will be understood that the bioremediation assembly 10 of the present invention includes a valve which is generally indicated by the numeral 80, and which is mounted on the outside facing surface 40 of the bioremediation reservoir 30. The valve 80, as depicted, is a two-way fluid directing valve which is positioned downstream of, and coupled in fluid flowing relation relative to, the exhaust end 66 of the inline heater 63. The valve has valve handle 81 which is movable between first and second positions 82 and 83, respectively. As seen in FIGS. 3 and 4, and in the first position 82, the valve 80 is operable to direct bioremediating fluid 54 which has been heated by the inline heater 63 through the valve body and into a fluid dispensing manifold as will be described hereinafter. Still further, the valve handle 81 is operable to move to a second position 83 as seen in FIGS. 5 and 6, and wherein, in the second position, the valve 80 is operable to direct bioremediating fluid 54 along a course of travel and into a fluid applicator as will also be discussed in the paragraphs which follow. The valve handle 81 is movable between the first position 82, and the second position 83 by an operator who is utilizing the bioremediation assembly 10. As should be understood, the valve 80 has a first fluid discharge outlet 84 which is operable to direct bioremediating fluid 54 out through the valve 80 and into a fluid dispensing manifold as will be discussed below. Still further, the valve 80 has a second fluid discharge outlet 85 which allows bioremediating fluid 54 to leave the valve 80 and travel to a fluid applicator where it will be dispensed on an object of interest as will be described in greater detail, hereinafter.

Referring still to FIGS. 3-9, a fluid dispensing manifold 90 is positioned within the cavity 42 of the bioremediation reservoir 30, and which is further located in spaced relation relative to the top surface 55 of the volume of aqueous bioremediating fluid 54 which is enclosed in the bioremediation reservoir 30. The fluid dispensing manifold 90 is coupled in fluid flowing relation relative to the pump 50, and is operable to direct a stream of bioremediating fluid, as will be described below, downwardly onto the top surface 55 of the volume of bioremediating fluid 54 so as to effectively aerate the volume of bioremediating fluid 54 to support the growth of the aerobic microorganisms which facilitate the bioremediation of the hydrocarbon substances which are received within same. In this regard, it will be seen that the fluid dispensing manifold 90 has a main body 91, with a first end 92, and an opposite second end 93. The first end 92 is positioned downstream of and coupled in fluid flowing relation relative to the first discharge opening 84 of the valve 80 by way of a third fluid conduit which is generally indicated by the numeral 94. As seen in the drawings, a plurality of apertures 95 are formed in the main body 91. The apertures form a plurality of streams of bioremediating fluid 96 (FIG. 3) which are directed downwardly onto the top surface 55 of the volume of bioremediating fluid 54 so as to create small, minute, and microscopic air bubbles 97 which are drawn downwardly through the volume of bioremediating fluid 54 by the action of the pump 50 and in the direction of the bottom panel or surface 37. This action by the pump which draws the air bubbles 97 downwardly causes a thorough and complete aeration of the bioremediating fluid 54. Still further, the streams of operating in an aeration mode, as seen in FIG. 3, substantially prevents the accumulation of any hydrocarbon substance on the top surface 55 of the bioremediating fluid 54. In the arrangement as seen in that view, the plurality of streams of bioremediating fluid 96 each have a fluid pressure of at least about 1.5 PSI.

Figure 9:
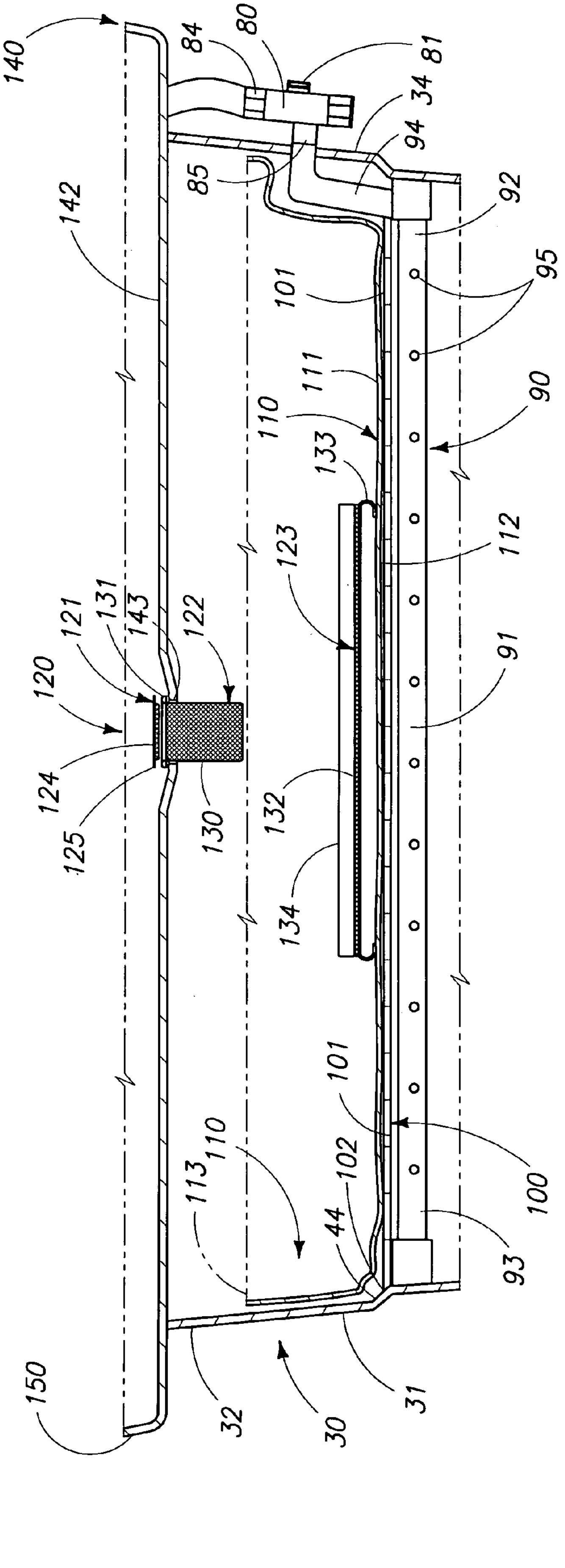
FIG. 9 is a fragmentary, transverse, vertical sectional view of a portion of the bioremediation assembly of the present invention.
Figure 10:
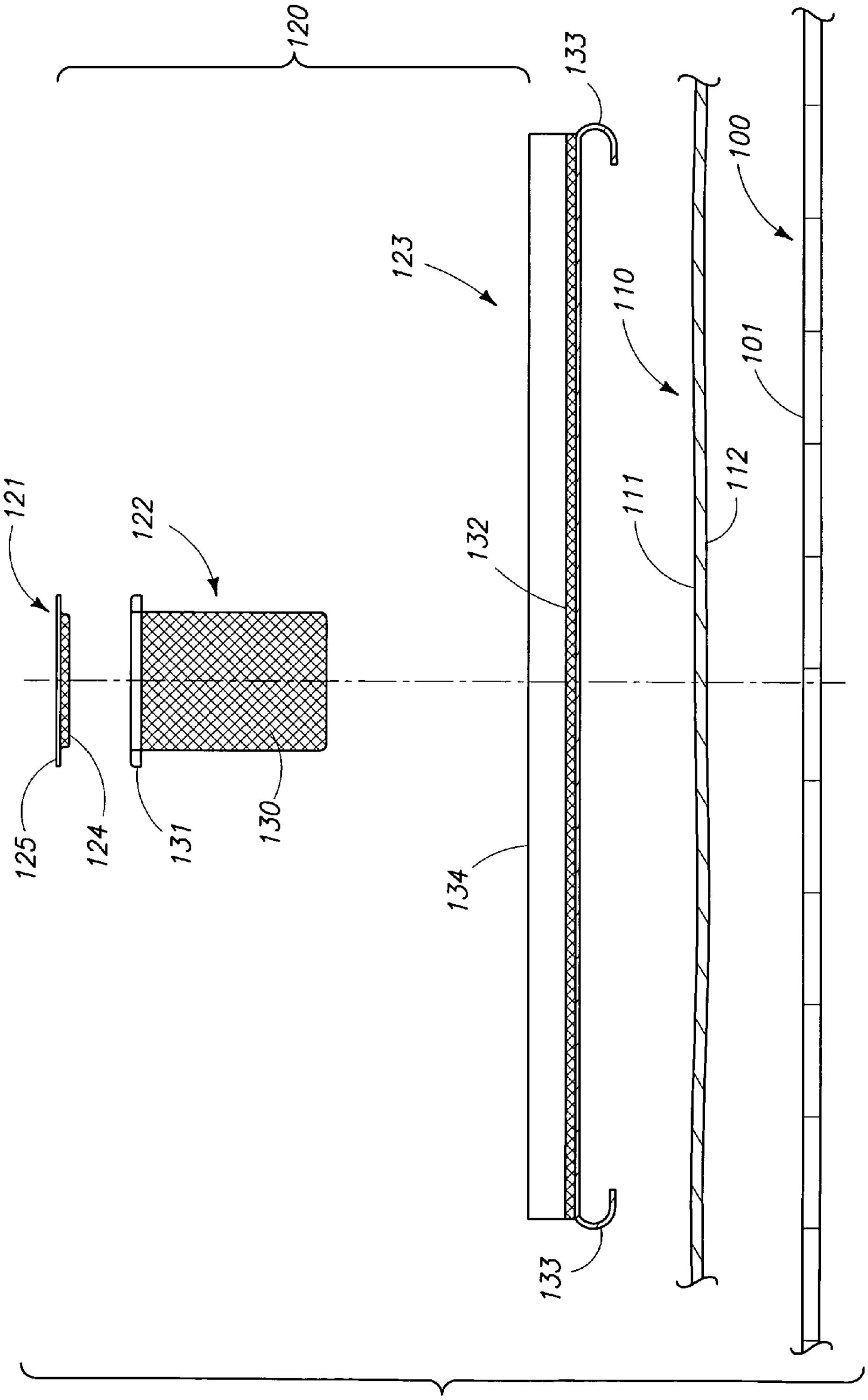
FIG. 10 is a fragmentary, exploded, transverse, vertical sectional view of a plurality of metal screen filters which are used in combination with a porous evaporation barrier in the bioremediation assembly of the present invention.

Mounted above, and upstream relative to the fluid dispensing manifold 90 is a supporting metal grid which is generally indicated by the numeral 100 (FIGS. 9 and 10). This supporting metal grid generally has apertures having a size of about 1 inch by 2 inches. The supporting metal grid 100 has a top surface 101 and a peripheral edge 102. The surface area of the supporting grid 100 is such that the grid is received within the cavity 42 of the bioremediating reservoir 30 and further rests upon the step or ledge 44 which is defined in the inside facing surface 41 thereof. The supporting metal grid is generally horizontally disposed, and is operable to support a porous evaporation barrier 110 in spaced, upstream and covering relation relative to the top surface 55 of the volume of bioremediating fluid 54 which is received in the bioremediating reservoir 30. In this regard, the porous evaporation barrier has a top surface 111, and a bottom, or inwardly facing surface 112 which facilitates the condensation of gaseous bioremediating fluid 54 thereon. The porous evaporation barrier 110 generally has a porosity of less than about 75 microns. As seen in the drawing, the porous evaporation barrier is a flexible sheet having a peripheral edge 113. The porous evaporation barrier is supported, in part, on the top surface 101 of the supporting metal grid, and may further lay, in part, against the inwardly facing surface 41 of the bioremediating reservoir 30 as seen in FIG. 9. The porous evaporation barrier 110, as indicated, causes the condensation of gaseous bioremediating fluid 54 and thereby prevents the premature loss of bioremediating fluid from the bioremediating reservoir 30 through normal evaporation, but further is porous so as to allow the passage of bioremediating fluid 54 which drains through the porous evaporation barrier after it has been previously dispensed on an object of interest that is being treated within the wash basin. This wash basin will be discussed in greater detail, below.

As best understood by a study of FIGS. 9 and 10, it will be understood that the bioremediation assembly 10 of the present invention includes a plurality of metal screen filters 130 which are positioned downstream of the wash basin drain which will be described hereinafter, and upstream of the opening 43 of the bioremediating reservoir 30, and which are individually operable to remove particulate matter which passes from the wash basin and through the drain thereof from the stream of bioremediating fluid which has been dispensed on an object of interest. As illustrated most clearly by references to FIGS. 9 and 10, the plurality of metal screen filters have a porosity which lie in a range of about 10 to about 40 one thousandths of an inch. Still further, it should be understood that the plurality of metal screen filters 130 have a decreasing porosity when the respective porosities of the metal screen filters are positioned or measured at increasing distances away from the drain of the wash basin, which will be described below. In this regard, the plurality of metal screen filters comprise first, second and third metal screen filters 121, 122 and 123, respectively. As best illustrated by references to FIGS. 9 and 10, the first metal screen filter 121 has a main body 124 which has a porosity of about 40 one thousandths of an inch. The main body is cup shaped, and further includes a circumscribing rim or flange 125 which is operable to rest in mating receipt thereagainst the second metal screen filter 122. The second metal screen filter 122 has a main body 130 which is formed into an elongated an inch. The inside diametral dimension of the second metal screen filter is larger than the outside diametral dimension of the main body 124 of the first metal screen filter 121 thereby allowing the first metal screen filter to be telescopingly received, at least in part, within the second metal screen filter 122. The second metal screen filter 122 has a circumscribing rim or flange 131 which is operable to rest thereagainst the drain of the wash basin which will be described below. Positioned in downstream relation relative to the second metal screen filter 122 is a third metal screen filter 123. The third metal screen filter has a porosity of about 10 one thousandths of an inch, and further is substantially horizontally oriented. In this regard, the third metal screen filter 123 has a main body 132 which is positioned in spaced relation relative to the porous evaporation barrier 110 by a pair of supporting legs 133. Still further, the main body 132 is surrounded by a substantially vertically disposed, and fluid impervious sidewall 134. As should be understood, the individual metal screen filters which have individual porosities of 40 one thousandths; 20 one thousandths; and 10 one thousandths of an inch, respectively, are operable to remove particulate matter from the bioremediating fluid 54 which drains from the wash basin as will be described below thereby removing particulate matter and preventing the contamination of the bioremediating fluid 54 which is contained within the reservoir 30.

Referring more particularly to FIG. 1 and following, the bioremediation assembly 10 of the present invention includes a wash basin which is generally indicated by the numeral 140. The wash basin includes a main body 141 which has a bottom supporting surface 142. A drain 143 is formed substantially centrally of the bottom supporting surface and which allows bioremediating fluid 54, containing particulate matter, to drain therefrom. As earlier discussed, the drain 143 cooperates with and is partially occluded by the second metal screen filter 122. The main body 130 of the second metal screen filter has an outside diametral dimension which is less than the inside diametral dimension of the drain 143. Therefore, the main body 130 is telescopingly received within the drain 143 and the circumscribing rim or flange 131 rests in supporting relation thereabout the drain as illustrated most clearly by reference to FIG. 9. As earlier described, the first metal screen filter 121 has a main body 124 which telescopes, at least in part, within the main body 130 of the second metal screen filter 122. The bottom supporting surface 142 has a leading peripheral edge 144 and a trailing peripheral edge 145 (FIG. 1). A pair of hinges 146 are fastened to the bottom supporting surface 142 near the trailing peripheral edge 145 and also to the first end 32 of the bioremediating reservoir 30. This permits the wash basin 140 to be moved out of draining or coaxial alignment relative to the upwardly facing opening 43, as seen in FIG. 1 so as to permit an operator to gain access to the cavity 42 so as to be able to remove the third metal screen filter 123, and the porous evaporation barrier 110. This arrangement also allows for the ready access to the volume of bioremediating fluid 54 for replenishment, replacement, and the like. Extending normally, upwardly relative to the bottom supporting surface 142 is a peripheral sidewall 150. The peripheral sidewall includes, in part, a leading sidewall 151, and a trailing sidewall 152. The peripheral sidewall 150 further defines a cavity 153 which is operable to contain bioremediating fluid 54 which has been dispensed within the wash basin 140 while treating an object of interest. As illustrated by reference to FIG. 1, a latch arrangement 154 is mounted on the leading sidewall 151 and on the first end 32 of the bioremediating reservoir 30. This permits the wash basin 140 to be releasably secured in an appropriate draining relationship relative to the bioremediating reservoir 30.

As seen most clearly by reference to FIG. 2 and following, the bioremediation assembly 10 includes a fluid applicator which is generally indicated by the numeral 160. As illustrated in the drawings, the fluid applicator may include a first fluid applicator 161, and a second fluid applicator 162. As illustrated, the first fluid applicator provides a nozzle providing a substantially unitary stream of bioremediating fluid 154 that may be supplied to an object of interest. Still further, the second fluid applicator 162 provides a flow-through scrubbing brush that may be used to scrub clean an object of interest. The first and second fluid applicators are coupled in fluid flowing relation relative to a two-way valve or faucet assembly 163. The two-way valve or faucet assembly 163 is coupled in fluid flowing relation relative to a fourth fluid conduit 164 (FIG. 3). The fourth fluid conduit 164 is coupled in downstream fluid flowing relation relative to the second discharge opening 85 of the valve 80. Therefore, bioremediating fluid 54 which has been released by the valve 80 may travel along the fourth fluid conduit 164 and then be directed as determined by the operator between the first fluid applicator 161, and the second fluid applicator 162. The two-way valve or faucet assembly 163 has a valve handle 165 which can be moved in order to direct the bioremediating fluid therebetween the first and second fluid applicators. The first and second fluid applicators are operable to direct a stream of bioremediating fluid against an object of interest 170, here illustrated as a gear, in order to remove hydrocarbon substances and other particulate matter which may be deposited on the object of interest 170. The bioremediating fluid including the hydrocarbon substance, and any particulate matter mixed with same thereafter is received through the plurality of metal screen filters where the particulate matter is removed, and the hydrocarbon substance which was deposited on the object interest 170 is treated by the bioremediating fluid 54. As seen, the plurality of metal screen filters which are positioned downstream of the wash basin drain 143 are adapted to remove increasing amounts of particulate matter thereby preventing particulate matter from reaching the porous evaporation barrier 110. The porous evaporation barrier 110 allows the passage of the bioremediating fluid 54 including the hydrocarbon substance so that it may be received within the bioremediating reservoir 30, and be treated by the bacteria that reside in same. As best seen by reference to FIG. 7, a convenient electrical GFCI outlet 180 is mounted on the bioremediating reservoir 30 and is operable to provide electrical power safely to the pump 50, and the inline heater 63. The electrical outlet 180 is coupled with a suitable source of 120 volt AC power, not shown.

OPERATION

The operation of the described embodiment of the present invention is believed to be readily apparent and is briefly summarized at this point.

A first aspect of the present invention relates to a bioremediation assembly 10 which includes a bioremediation reservoir 30 defining a cavity 42 and which encloses a volume of an aqueous bioremediating fluid 54 at a predetermined temperature. The bioremediation reservoir 30 has a geometry which acts upon the volume of the aqueous bioremediating fluid 54 so as to cause the bioremediating fluid to be maintained at a substantially constant temperature. The bioremediation assembly further includes a pump 50 mounted within the bioremediation reservoir 30, and which is operable to remove the aqueous bioremediating fluid 54 from the bioremediation reservoir 30. Still further, a fluid dispensing manifold 90 is provided, and which is positioned within the cavity 42 of the bioremediation reservoir 30 and located in spaced relation relative to a top surface 55 of the volume of aqueous bioremediating fluid 54 which is enclosed with the bioremediation reservoir 30. The fluid dispensing manifold 90 is coupled in fluid flowing relation relative to the pump 50, and is operable to direct a stream of bioremediating fluid 96 downwardly into the top surface 55 of the bioremediating fluid 54 so as to aerate the volume of bioremediating fluid 54. In the arrangement as seen in the drawings, the bioremediating fluid 54 is maintained at a temperature of about 105 degrees F. to about 115 degrees F., and the stream of bioremediating fluid 96 comprises a plurality of streams of fluid which each have a pressure of at least about 1.5 PSI. In the arrangement as seen in FIG. 1 and following, the bioremediation reservoir 30 has a first end 32, and an opposite second end 33. The bioremediation reservoir 30 has a diminishing cross sectional dimension when that cross sectional dimension is measured from the first end, in the direction of the second end. Still further, the bioremediation reservoir has a first portion 35 which is defined by a substantially vertically disposed sidewall 34, and a second portion 36 which is made integral with the first portion. The second portion, which is defined by a sidewall 34, slopes inwardly toward a substantially flat bottom panel 37, and the pump 50 is mounted on the substantially flat bottom panel. The above-mentioned geometry is believed to encourage the thorough circulation of the bioremediating fluid 54 through the reservoir 30. This complete circulation facilitates uniformity of temperature and aeration throughout the volume of the bioremediating fluid 54. In addition to the foregoing, the bioremediation assembly 10 includes an in-line heater 63 which is coupled in downstream fluid flowing relation relative to the pump 50, and which is further located upstream relative to the fluid manifold 90, and which is further mounted on an outside facing surface 40 of the bioremediation reservoir 30. The in-line heater 63 heats the bioremediating fluid 54 as the bioremediating fluid is pumped from the bioremediation reservoir 30 to the fluid dispensing manifold 90. As earlier disclosed, the in-line heater 63 has a fluid pressure sensor (not shown) which is operable to render the in-line heater inoperable unless the fluid pressure sensor senses a given fluid pressure as provided by the volume of bioremediating fluid 54. The bioremediation assembly 10 further includes a porous evaporation barrier 110 which is positioned in covering relation relative to the opening 43 which is defined by the bioremediation reservoir 30, and which impedes, at least in part, the evaporation of the bioremediating fluid 54 from the bioremediation reservoir 30. The porous evaporation barrier has an inwardly facing surface 112 which facilitates the condensation of gaseous bioremediating fluid 54 thereon, and an opposite, outwardly facing surface 111. The porosity of the porous evaporation barrier is less than about 75 Microns.

The bioremediation reservoir 10 of the present invention includes a wash basin 140 having a drain 143 which is mounted in upstream fluid draining communication with the bioremediation reservoir 30. Still further, a fluid applicator 160 is provided and which is mounted in fluid dispensing relation relative to the wash basin 140 and which is further coupled in downstream fluid flowing relation relative to the pump 50. The fluid applicator 160 dispenses bioremediating fluid 54 which has been provided by the pump 50, and previously heated by the in-line heater 63, into the wash basin 140 to wash an object of interest 170. The object of interest 170 may occasionally produce particulate matter. As seen in the drawings, a plurality of fluid applicators 161 and 162 may be provided. In addition to the foregoing, the bioremediation assembly 10 includes a plurality of metal screen filters 120 which are generally positioned downstream of the wash basin drain 143, and upstream of the opening 43 of the bioremediation reservoir 30. The plurality of metal screen filters 120 removes particulate matter which passes from the wash basin 140 and through the drain 143 thereof. The plurality of metal screen filters 120 have a porosity which lie in a range of about 10 to about 40 one thousandths of an inch. The plurality of metal screen filters 120 have a decreasing porosity when the respective metal screen filters are positioned at increasing distances away from the drain 143 of the wash basin 140. In the arrangement as seen in the drawings, the object of interest 170 is coated, at least in part, with a hydrocarbon substance which is washed from the object of interest by the bioremediating fluid 54 which is delivered by one of the fluid applicators 160. The hydrocarbon substance which is removed from the object of interest is received in the cavity 42 of the bioremediation reservoir 30. The streams of bioremediating fluid 96 which are directed downwardly onto the top surface 55 of the bioremediating fluid 54 by the fluid dispensing manifold 90 while the invention 10 is operating in an aeration mode, substantially prevents the accumulation of any coagulated hydrocarbon substances on the top surface 55 of the bioremediating fluid 54, as well as creating small air bubbles 97 which are drawn downwardly through the volume of the bioremediating fluid 54 by the action of the pump 50, and in the direction of the bottom panel 37 so as to appropriately aerate the bioremediating fluid so as to encourage the growth of the aerobic microorganisms which are contained therein and which degrade the hydrocarbon substance. In addition to the foregoing, the bioremediation assembly 10 of the present invention includes a valve 80 which is positioned in selective fluid metering relation relative to the fluid applicators 160, and the fluid dispensing manifold 90. The valve 80 is located downstream relative to the inline heater 63. The valve 80 has a first position 82 which allows heated bioremediating fluid 54 which has been withdrawn by the pump 50 to be delivered solely to the fluid dispensing manifold 90; and a second position 83 which allows bioremediating fluid to be delivered solely to the fluid applicator 160.

The present invention also relates to a method for bioremediation. The present method broadly includes the steps of providing an object of interest 170 which is coated with a hydrocarbon substance; providing a source of bioremediating fluid 54 which has a top surface 55; and withdrawing a portion of the bioremediating fluid 54 and forming a stream of bioremediating fluid 96 which alternatively is directed downwardly against the top surface 55 of the bioremediating fluid 54 so as to form small air bubbles 97, or which is directed against the object of interest 170 so as remove the hydrocarbon substance from the object of interest and remediate same.

More specifically, the method for bioremediation of the present invention includes the steps of providing a bioremediation reservoir 30 with a bottom surface 37, and an upwardly facing opening 43, and which further has a predetermined geometry which defines an internal cavity 42. The method further includes the step of supplying a source of a bioremediating fluid 54 to the bioremediation reservoir 30, and wherein the bioremediating fluid has a top surface 55. The method further includes a step of providing a wash basin 140 which is located in gravity draining relation relative to the opening 43 of the bioremediation reservoir 30. The method includes another step of providing a fluid applicator 160 which is mounted on the wash basin 140, and further providing a fluid dispensing manifold 90 and positioning the fluid dispensing manifold in spaced, fluid dispensing relation relative to the top surface 55 of the bioremediating fluid 54, and downstream relative to the wash basin 140. The method includes another step of providing a pump 50 which is mounted on the bottom surface 37 of the bioremediation reservoir 30 and which withdraws the bioremediating fluid 54 from the bioremediation reservoir 30. The method includes yet another step of providing a heater 63 for heating the bioremediating fluid 54 to a given temperature, and which is coupled in fluid receiving relation relative to the pump 50. The method includes yet another step of providing a valve assembly 80 which is coupled in fluid receiving relation relative to the heater 63 and which is further disposed in selective upstream fluid dispensing relation to the fluid dispensing manifold 90 and the fluid applicators 160. The method includes another step of providing and positioning a porous evaporation barrier 110 in substantially covering relation relative to the opening 43 of the bioremediation reservoir 30, and upstream of the fluid dispensing manifold 90. Still further, the method includes another step of withdrawing the bioremediating fluid, 54 from the bioremediation reservoir 30 with the pump 50, and alternatively delivering the heated bioremediation fluid 54 to the fluid dispensing manifold 90, or to one of the fluid applicators 160.

The methodology as described above includes yet another step of providing a plurality of serially arranged metal screen filters 120 which have individually decreasing porosities, and positioning the plurality of serially arranged metal screen filters downstream of the wash basin 140, and upstream relative to the porous evaporation barrier 110. In addition to the foregoing, the method includes another step of providing a fluid pressure sensor which is mounted on the in-line heater 63, and which senses the fluid pressure of the bioremediating fluid 54 within the bioremediation reservoir 30. In the methodology as described above, the step of withdrawing the bioremediating fluid 54 from the bioremediation reservoir 30 and delivering the heated bioremediating fluid to the fluid dispensing manifold 90 further includes the step of directing a plurality of streams of bioremediating fluid 96 downwardly from the fluid dispensing manifold 90 onto the top surface 55 of the bioremediating fluid 54 so as to create small, to microscopic, air bubbles 97 in the bioremediating fluid 54 which facilitates the effective aeration of the bioremediating fluid 54, and which further, on the one hand, inhibits the accumulation, or on the other hand, facilitates the dispersion of any hydrocarbon substance floating on the top surface 55 of the bioremediating fluid 54. In the methodology as described above, the step of providing the bioremediation reservoir 30 having the predetermined geometry which defines an internal cavity 42 further includes the step of reducing the cross sectional dimensions of internal cavity 42 as that is measured from the opening 43, as defined by the bioremediation reservoir 30, in the direction of the bottom surface 37 thereof. In the arrangement as seen, the step of providing a heater further includes the step of positioning the heater 63 outside of the internal cavity 42 of the bioremediation reservoir 30. As should be understood, the heater 63 comprises an in-line heater which heats the bioremediating fluid 54 in the bioremediation reservoir 30 to a temperature of about 105 degrees F. to about 115 degrees F. In the method as described, above, the step of providing and positioning a porous evaporation barrier upstream of the fluid dispensing manifold 90 further includes the step of providing a porous evaporation barrier 110 which has a porosity of less than about 75 Microns and which is operable to impede the evaporation of the bioremediating fluid 54 from the bioremediation reservoir 30.

Therefore, it will be seen that the bioremediation assembly 10 and methodology for bioremediation, as described herein, provides a convenient means whereby hydrocarbon substances, and particulate matter which are dislodged from objects of interest which are being cleaned within the wash basin 140 may be conveniently and environmentally bioremediated in a fashion not possible heretofore, and which further addresses many of the shortcomings attendant with the prior art practices and devices utilized for substantially identical purposes.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. A bioremediation assembly, comprising:

a bioremediation reservoir defining a cavity and which encloses a volume of an aqueous bioremediating fluid at a predetermined temperature, and wherein the bioremediation reservoir has a geometry which acts upon the volume of the aqueous bioremediating fluid so as to cause the bioremediating fluid to be maintained at a substantially constant temperature, and wherein the bioremediation reservoir has a first portion which is defined by a substantially vertically disposed sidewall, and which further defines an opening, and a second portion which is made integral with the first portion, and which is further defined by a sidewall which slopes inwardly toward a substantially flat bottom panel;

a wash basin having a drain which is mounted in fluid flowing communication with the opening of the bioremediation reservoir;

a pump mounted within the bioremediation reservoir and which is operable to remove the aqueous bioremediating fluid from the bioremediation reservoir and wherein the pump is mounted on the substantially flat bottom panel;

a fluid dispensing manifold positioned within the cavity of the bioremediation reservoir and located in spaced relation relative to a top surface of the volume of aqueous bioremediating fluid which is enclosed with the bioremediation reservoir, and wherein the fluid dispensing manifold is coupled in fluid flowing relation relative to the pump, and is operable to direct a stream of bioremediating fluid downwardly into the top surface of the bioremediating fluid so as to aerate the volume of bioremediating fluid;

an in-line heater which is coupled in fluid flowing relation relative to the pump and the fluid manifold, and which is further mounted on an outside facing surface of the bioremediation reservoir, and wherein the in-line heater heats the bioremediating fluid as the bioremediating fluid is pumped from the bioremediation reservoir to the fluid dispensing manifold; and a plurality of metal screen filters positioned downstream of the wash basin drain, and upstream of the opening of the bioremediation reservoir and which removes particulate matter which passes from the wash basin and through the drain thereof.

2. A bioremediation assembly as claimed in claim 1, and wherein the bioremediating fluid is maintained at a temperature of about 105 degrees F. to about 115 degrees F.

3. A bioremediation assembly as claimed in claim 1, and wherein the stream of fluid comprises a plurality of streams of fluid which each have a pressure of at least about 1.5 PSI.

4. A bioremediation assembly as claimed in claim 1, and wherein the in-line heater has a fluid pressure sensor which is operable to render the in-line heater inoperable unless the fluid pressure sensor senses a given fluid pressure as provided by the volume of bioremediating fluid.

5. A bioremediation assembly as claimed in claim 1, and wherein the opening defined by the bioremediation reservoir allows fluid flowing communication with the bioremediating fluid which is enclosed within the cavity of the bioremediation reservoir, and wherein the bioremediation assembly further comprises:

a porous evaporation barrier positioned in covering relation relative to the opening defined by the bioremediation reservoir and which impedes, at least in part, the evaporation of the bioremediating fluid from the bioremediation reservoir.

6. A bioremediation assembly as claimed in claim 5, and wherein the porous evaporation barrier has an inwardly facing surface which facilitates the condensation of gaseous bioremediating fluid thereon, and an opposite, outwardly facing surface, and wherein the porosity of the porous evaporation barrier is less than about 75 Microns.

7. A bioremediation assembly as claimed in claim 1, and wherein the opening defined by the bioremediation reservoir allows fluid flowing communication with the bioremediating fluid which is enclosed within the cavity of the bioremediation reservoir, and wherein the bioremediation assembly further comprises:

a fluid applicator mounted in fluid dispensing relation relative to the wash basin and which is further coupled in fluid flowing relation relative to the pump, and wherein the fluid applicator dispenses bioremediating fluid into the wash basin to wash an object of interest, and wherein the object of interest when washed produces particulate matter.

8. A bioremediation assembly as claimed in claim 7, and wherein the fluid applicator comprises plural fluid applicators.

9. A bioremediation assembly as claimed in claim 7, and wherein the object of interest is coated, at least in part, with a hydrocarbon substance which is washed from the object of interest by the bioremediating fluid which is delivered by the fluid applicator, and wherein the hydrocarbon substance which is removed from the object of interest is received in the cavity of the bioremediation reservoir; and wherein the steam of bioremediating fluid which is directed downwardly onto the top surface of the bioremediating fluid by the fluid dispensing manifold substantially prevents the accumulation of any coagulated hydrocarbon substance on the top surface of the bioremediating fluid.

10. A bioremediation assembly as claimed in claim 1, and wherein the plurality of metal screen filters have a porosity which lie in a range of about 10 to about 40 one thousandths of an inch.

11. A bioremediation assembly as claimed in claim 10, and wherein the plurality of metal screen filters have a decreasing porosity when the respective metal screen filters are positioned at increasing distances away from the drain of the wash basin.

12. A bioremediation assembly, comprising:

a bioremediation reservoir defined by a continuous sidewall, and a bottom panel which is made integral with the continuous sidewall, and wherein the continuous sidewall defines an upwardly oriented opening, and an internal cavity, and wherein the bioremediation reservoir has a cross sectional dimension which diminishes when measured in a direction extending from the opening of the bioremediation reservoir in the direction of the bottom panel thereof;

a volume of bioremediating fluid received within the internal cavity of the bioremediation reservoir, and wherein the bioremediating fluid has a top surface;

a pump mounted on the bottom panel and within the internal cavity of the bioremediation reservoir, and wherein the pump withdraws bioremediating fluid from the bioremediation reservoir;

a wash basin having a drain which is mounted in fluid communication with the opening which is defined by the bioremediation reservoir;

a porous evaporation barrier positioned in covering relation relative to the opening of the bioremediation reservoir and which inhibits, at least in part, the evaporation of the bioremediating fluid from the bioremediation reservoir;

a plurality of metal filters having a decreasing porosity, and which are positioned downstream of the wash basin and upstream relative to the porous evaporation barrier;

a fluid applicator positioned in fluid dispensing relation relative to the wash basin;

an in-line heater mounted on an outside facing surface of the continuous sidewall, and wherein the in-line heater is coupled in fluid communication with the pump and with fluid applicator, and wherein the heater is located upstream relative to the pump and is operable to heat the bioremediating fluid, and is further located downstream relative to the fluid applicator; and a fluid dispensing manifold mounted within the internal cavity of the bioremediation reservoir and in spaced relation relative to the top surface of the bioremediating fluid, and wherein the fluid dispensing manifold is coupled in fluid flowing relation relative to the pump, and is located downstream relative to the in-line heater, and wherein the fluid dispensing manifold, when operated in an aeration mode, directs a plurality of streams of bioremediating fluid downwardly onto the top surface of the bioremediating fluid so as create small air bubbles which are drawn downwardly through the volume of the bioremediating fluid by the action of the pump and in the direction of the bottom panel.

13. A bioremediation assembly as claimed in claim 12, and wherein the fluid applicator includes two fluid applicators.

14. A bioremediation assembly as claimed in claim 12, and wherein the in-line heater imparts heat energy to the bioremediating fluid, and wherein the bioremediation reservoir facilitates the circulation of the bioremediating fluid within the internal cavity of the bioremediation reservoir so that the bioremediating fluid has a substantially uniform temperature of about 105 degrees F. to about 115 degrees F. substantially throughout the entire volume of the bioremediating fluid.

15. A bioremediation assembly as claimed in claim 12, and wherein the continuous sidewall is defined by a first portion which is substantially vertically oriented and a second portion which is frustum shaped.

16. A bioremediation assembly as claimed in claim 12, and further comprising:

a valve positioned in fluid metering relation relative to the fluid applicator, and the fluid dispensing manifold, and which is further located downstream relative to the in-line heater, and wherein the valve has a first position which allows bioremediating fluid to be delivered solely to the fluid dispensing manifold, and a second position which allows bioremediating fluid to be delivered solely to the fluid applicator.

17. A bioremediation assembly as claimed in claim 12, and wherein the porous evaporation barrier has an inwardly facing surface which facilitates the condensation of gaseous bioremediating fluid thereon, and an opposite, outwardly facing surface, and wherein the porosity of the porous evaporation barrier is less than about 75 Microns.

18. A bioremediation assembly as claimed in claim 12, and wherein the in-line heater is fluid pressure sensitive, and further maintains the bioremediating fluid at a temperature of about 105 degrees F. to about 115 degrees F.

19. A bioremediation assembly as claimed in claim 12, and wherein the fluid applicator applies a stream of bioremediating fluid to an object of interest which is coated, at least in part, by a hydrocarbon substance, and wherein hydrocarbon substance is removed from the object of interest and is received into the bioremediation reservoir for bioremediation by the bioremediating fluid, and wherein the stream of bioremediating fluid which is delivered by the fluid dispensing manifold, when in the aeration mode, substantially prevents the accumulation of any hydrocarbon substance on the top surface of the bioremediating fluid.

20. A bioremediation assembly as claimed in claim 12, and wherein the bioremediating fluid has an aerobic microbial population, and wherein fluid dispensing manifold creates a sufficient number of small and microscopic air bubbles so as ensure the proper aeration of the aerobic microbial population.

21. A bioremediation assembly as claimed in claim 12, and wherein the plurality of metal filters have a porosity which lie in a range of about 10 to about 40 one thousandths of an inch.

22. A bioremediation assembly as claimed in claim 12, and wherein fluid dispensing manifold delivers the plurality of streams of bioremediating fluid at a pressure of greater than about 1.5 PSI.

* * * * *

UNITED STATES PATENT AND TRADEMARK OFFICE

CERTIFICATE OF CORRECTION

PATENT NO. : 7,303,908 B1
APPLICATION NO. : 11/495275
DATED : December 4, 2007
INVENTOR(S) : Bert Overland It is certified that error appears in the above-identified patent and that said Letters Patent is hereby corrected as shown below:

Column 6, line 38, replace “of operating” with --of bioremediation fluid 96, which are delivered by the fluid dispensing manifold 90, when operating--.

Column 7, line 39, replace “elongated an inch” with --cylindrical shape, as illustrated and which has a porosity of about 20 one thousandths of an inch.--.

Signed and Sealed this

Eighth Day of July, 2008

JON W. DUDAS
*Director of the United States Patent and Trademark Office*